United States Patent
Lane et al.

(10) Patent No.: US 11,980,666 B2
(45) Date of Patent: May 14, 2024

(54) PRESERVATIVE SYSTEMS

(71) Applicant: Alumier Labs, Inc., North York (CA)

(72) Inventors: Sanford Lane, Sherborn, MA (US);
Irwin Palefsky, West Orange, NJ (US);
Yamaris Malendez, Clifton, NJ (US);
Wanda Fontaine, Plainfield, NJ (US);
Nadera Rickford, Toronto (CA)

(73) Assignee: Alumier Labs, Inc., North York (CA)

( * ) Notice: Subject to any disclaimer, the term of this patent is extended or adjusted under 35 U.S.C. 154(b) by 0 days.

(21) Appl. No.: 15/983,488

(22) Filed: May 18, 2018

(65) Prior Publication Data

US 2018/0333494 A1 Nov. 22, 2018

Related U.S. Application Data

(60) Provisional application No. 62/508,594, filed on May 19, 2017.

(51) Int. Cl.

| | | |
|---|---|---|
| *A61K 47/26* | (2006.01) | |
| *A61K 8/34* | (2006.01) | |
| *A61K 8/37* | (2006.01) | |
| *A61K 8/60* | (2006.01) | |
| *A61K 9/00* | (2006.01) | |
| *A61K 31/047* | (2006.01) | |
| *A61K 31/08* | (2006.01) | |
| *A61K 31/23* | (2006.01) | |
| *A61K 31/351* | (2006.01) | |
| *A61K 45/06* | (2006.01) | |
| *A61K 47/10* | (2017.01) | |
| *A61Q 5/00* | (2006.01) | |
| *A61Q 5/02* | (2006.01) | |
| *A61Q 11/00* | (2006.01) | |
| *A61Q 15/00* | (2006.01) | |
| *A61Q 17/04* | (2006.01) | |
| *A61Q 19/00* | (2006.01) | |
| *A61Q 19/02* | (2006.01) | |

(52) U.S. Cl.
CPC ............. *A61K 47/26* (2013.01); *A61K 8/345* (2013.01); *A61K 8/375* (2013.01); *A61K 8/60* (2013.01); *A61K 8/604* (2013.01); *A61K 9/0014* (2013.01); *A61K 31/047* (2013.01); *A61K 31/08* (2013.01); *A61K 31/23* (2013.01); *A61K 31/351* (2013.01); *A61K 45/06* (2013.01); *A61K 47/10* (2013.01); *A61Q 5/006* (2013.01); *A61Q 5/02* (2013.01); *A61Q 11/00* (2013.01); *A61Q 15/00* (2013.01); *A61Q 17/04* (2013.01); *A61Q 19/00* (2013.01); *A61Q 19/02* (2013.01); *A61K 2800/524* (2013.01)

(58) Field of Classification Search
CPC ...... A61K 31/047; A61K 31/08; A61K 31/23; A61K 31/351; A61K 45/06; A61K 47/10; A61K 47/26; A61K 8/345; A61K 8/375; A61K 8/60; A61K 8/604; A61K 9/0014; A61K 2300/00; A61K 2800/524; A61Q 11/00; A61Q 15/00; A61Q 17/04; A61Q 19/00; A61Q 19/02; A61Q 5/006; A61Q 5/02
See application file for complete search history.

(56) References Cited

FOREIGN PATENT DOCUMENTS

| | | |
|---|---|---|
| EP | 2902009 A1 | 8/2015 |
| KR | 2015-0038852 A | 4/2015 |
| KR | 2015-0062394 A | 6/2015 |
| KR | 2017-0038582 A | 4/2017 |
| WO | WO-2010/046726 A1 | 4/2010 |

OTHER PUBLICATIONS

International Search Report and Written Opinion for International Application No. PCT/IB2018/000779, dated Sep. 28, 2018 (14 pages).
Chemyunion Presentation titled "Hebeatol Plus: Natural protection to your formula" (21 pages).
Product Bulletin: Lexgard® O. www.inolex.com (1 page).
Sensiva® SC 10 product description. Schülke&Mayr GmbH. (6 pages).
Sensiva® SC 50 product information. Schülke&Mayr GmbH. (6 pages).

*Primary Examiner* — Lezah Roberts
(74) *Attorney, Agent, or Firm* — Clark & Elbing LLP

(57) ABSTRACT

Described herein are preservative systems that can include xylitol esters and/or ethers, caprylyl glycol, ethylhexylglycerin, and 1,3-propanediol. Also disclosed are formulations such as cosmetics, pharmaceuticals, and personal care products that include a preservative system as described herein.

19 Claims, No Drawings

PRESERVATIVE SYSTEMS

CROSS REFERENCE TO RELATED APPLICATIONS

This application claims the benefit of Provisional Application Ser. No. 62/508,594, filed May 19, 2017, the contents of which are hereby entirely incorporated herein by reference.

FIELD OF THE INVENTION

This invention relates to combinations of chemical compounds that are useful in protecting various formulations, including cosmetics and personal care products, from microbial contamination.

BACKGROUND OF THE INVENTION

Microbial contamination can adversely affect the quality of pharmaceuticals, cosmetics, and personal care items by causing phase separations, odors, discoloration, and other unappealing changes, but more importantly, the contamination can pose health risks to consumers. Despite recommendations, consumers often fail to close and store products as they should, and they may also use or continue to use products long after any recommended date. Accordingly, there remains a need for safe and effective preservative systems, and consumers are increasingly concerned about systems that include ingredients that are not derived from natural sources, and that have irritating or hypersensitizing effects.

SUMMARY OF THE INVENTION

In one aspect, the present invention features preservative systems that include a xylitol ester and/or xylitol ether, caprylyl glycol, ethylhexylglycerin, and 1,3-propanediol. The preservative systems can be formulated as such. That is, the present invention encompasses compositions constituting a preservative system per se. The preservative systems can also be incorporated into an end-use formulation for administration to a mammal, and these end-use formulations are also within the scope of the present invention. Where the preservative systems are formulated as such, they may be packaged within a kit with instructions for use. Accordingly, the invention features kits in which a preservative system is prepared and packaged for convenient addition to a formulation suitable for use by a consumer or other end-user. As discussed further below, the invention therefore encompasses products, such as pharmaceutical, cosmetic, and personal care products that include a preservative system as described herein.

In some embodiments, the preservative system can also include an alkaloid, an amino acid residue, a steroid, a flavanoid, a flavonoid, a curcuminoid, a coumarin, a quinone, a phenolic compound, a polyphenolic compound, a glycoprotein, a carbohydrate, a terpene, a protein or peptide, or any combination thereof.

In some embodiments, the preservative system can also include anisic acid, butylene glycol, caprylhydroxamic acid, a chelating agent, chlorphenesin, dehydroacetic acid, gluconolactone, glycerin, glyceryl caprylate, glyceryl laurate, glyceryl undecylenate, 1,2-hexanediol, lactoferrin, nisin, pentylene glycol, phenylethyl alcohol, phenoxyethanol, phenylpropanol, polyaminopropyl biguanide, potassium sorbate, propylene glycol, sodium benzoate, sodium dehydroacetate, or any combination thereof. The chelating agent can be, for example, ethylenediaminetetraacetic acid (EDTA), disodium EDTA, trisodium EDTA, tetrasodium EDTA, sodium phytate, or a combination thereof.

All of the preservative systems of the invention and all formulations in which they are included are non-naturally occurring products. However, the xylitol esters of the invention are derived from natural products by chemical synthesis.

In some embodiments, the preservative system or the formulation of which it is a part is formulated for parenteral administration (e.g., non-oral administration such as topical, subcutaneous, or subdermal administration).

The xylitol ester or xylitol ether can conform to one or more of the structural formulas:

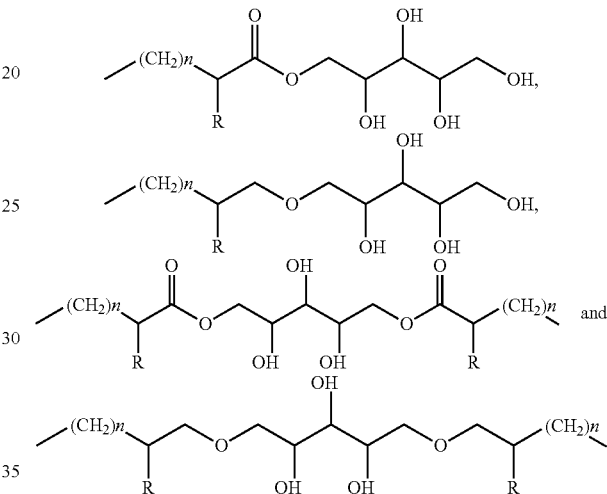

where R is H, $CH_3$, $CH_2CH_3$, or $CH_2(CH_2)y\text{-}CH_3$, with y being 1 to 15, inclusive, and n being, independently, 1-22, inclusive.

In some embodiments, the xylitol ester or xylitol ether (or combination thereof) is present in the final formulation at about 0.1-2.5% (w/w); the caprylyl glycol is present in the final formulation at about 0.25-3.0% (w/w); the ethylhexylglycerine is present in the final formulation at about 0.1-2.0% (w/w); and the 1,3-propanediol is present in the final formulation at about 1.0-10.0% (w/w). It is to be understood that any values within the ranges provided are within the scope of the present invention. For example, by stating that the xylitol ester or xylitol ether can be present in the final formulation at about 0.1-2.5% (w/w) we mean that the formulation can include, for example, 0.1-0.2%, 0.1-0.3%, 0.1-0.4% . . . 0.1-2.5%, 0.2-0.3%, 0.2-0.4% . . . 0.2-2.5%, 0.3-0.4%, 0.3-0.5%, 0.3-0.6% . . . 0.3-2.5% and . . . 0.24-0.25%.

In some embodiments, the xylitol ester or xylitol ether is present in the final formulation at 1.0% (w/w); the caprylyl glycol is present in the final formulation at 0.70% (w/w); the ethylhexylglycerine is present in the final formulation at 0.3% (w/w); and the 1,3-propanediol is present in the final formulation at 3.0% (w/w).

In some embodiments, the xylitol ester is xylityl sesquicaprylate or a combination of xylitol and caprylic acid.

The preservative systems described herein and/or the formulations of which they are a part can further include an active ingredient (e.g., a pharmaceutical or cosmetic agent (e.g., a pigment or dye).

The preservative systems per se and/or the formulations of which they are a part can be formulated as an emulsion, gel, liquid, ointment, stick, or serum. Formulations of which the preservative systems can be a part include, but are not limited to, analgesics, antacids, antihistamines antiperspirants, antiseptics (including antifungal and antibacterial products), antitussives, astringents, bronchodilators, cold sore remedies, counterirritants, demulcents, diaper rash creams, diuretics, expectorants, keratolytics, laxatives, moisturizers, mouthwashes, muscle relaxants, nasal decongestants, shampoos, sleep aids, sunscreens, and wound cleansers.

In any of the embodiments described herein, the preservative system can include, either instead of 1,3-propanediol or in addition to 1,3-propanediol, a glycol such as propylene glycol or pentylene glycol.

Aspects may have one or more of the following advantages.

Among other advantages, the formulation has the advantage of acting as an effective preservative with reduced toxic or irritating effects and less likelihood of causing allergic reactions compared to more commonly used ingredients such as parabens and formaldehyde.

DETAILED DESCRIPTION

Ingredients:

The preservative systems of the invention can include xylitol esters and/or ethers, caprylyl glycol, ethylhexylglycerin, and 1,3-propanediol. In some examples, the xylitol ester includes xylityl sesquicaprylate or a combination of xylitol and caprylic acid. In addition to these ingredients, the preservative systems can include benzyl alcohol. Alternatively or in addition, the preservative systems can include one or more alkaloids, amino acid residues, steroids, flavanoids, flavonoids, curcuminoids, cumarins, quinones, phenolic compounds, polyphenolic compounds, glycoproteins, carbohydrates, terpenes, proteins or peptides, or any combination thereof. In some embodiments, in addition to one or more xylitol esters and/or ethers, caprylyl glycol, chlorphenesin, ethylhexylglycerin, and 1,3-propanediol, the preservative systems can include anisic acid, butylene glycol, gluconolactone, glycerin, glyceryl caprylate, glyceryl undecylenate, lactoferrin, nisin, phenylethyl alcohol, phenoxyethanol, phenyl propanol, sodium benzoate, or any combination thereof.

The xylitol esters and ethers can conform to one or more of the structural formulas:

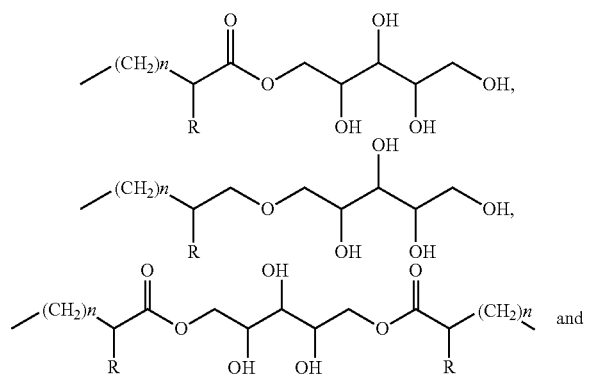

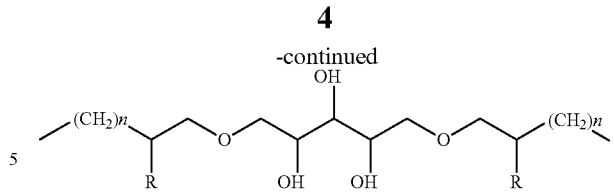

where R is H, $CH_3$, $CH_2CH_3$, or $CH_2(CH_2)y\text{-}CH_3$, with y being 1 to 15, inclusive, and n being, independently, 1-22, inclusive.

With regard to amounts, the xylitol ester or xylitol ether can be present in the final formulation at about 0.1-2.5% (w/w) (e.g., about 1.0-1.5%); the caprylyl glycol can be present in the final formulation at about 0.25-3.0% (w/w) (e.g., about 0.5-1.5% or about 0.75-1.0%); the ethylhexylglycerine can be present in the final formulation at about 0.1-2.0% (w/w) (e.g., about 0.1-1.0% or about 0.25-0.75%); and the 1,3-propanediol can be present in the final formulation at about 1.0-10.0% (w/w) (e.g., 2.0-4.0% or about 7.5%). Our work to date indicates that there may be advantages to varying the amounts of these ingredients with regard to one another depending on whether the intended formulation is an emulsion, liquid, serum, stick, or gel. Accordingly, the invention encompasses formulations in which one or more of the ingredients just recited are included in the upper half (e.g., at least the upper half, 60th %, 70th %, 75th %, 80th %, 85th %, 90th %, or 95th % of the value ranges just listed. These formulations include those that comprise surfactants, particularly biodegradable surfactants, amino acids, peptides, or proteins, sugars, water, particularly high concentrations of water (e.g., 20% or more) or formations that are intended to be mixed with water (e.g., facial cleansers or masks)

By "about" we mean plus-or-minus 10%. For example, about 1.0% is 0.9-1.1%, inclusive.

A preservative system that "protects" a product from microbial contamination is one that inhibits the growth of any given type of microorganism (e.g., a bacterium, virus, fungus, mold, or parasite) or any given microorganism (e.g., *E. coli, S. aureus*, or *C. albicans*) in the product. The preservative system may also, but does not necessarily, kill contaminating microorganisms. The preservative system may also have one or more of the following attributes: stability, compatibility with other ingredients in the formulations of which it is a part, utility at low concentrations, broad spectrum activity, and tolerability. Preferably, the preservative system is hypoallergenic.

A preservative system described herein may also be further characterized by the ingredients it excludes. For example, the preservative systems may be free of formaldehydes or compounds that release formaldehyde (e.g., formaldehyde (methanol), quaternium-15, imidazolidinyl urea, diazolidinyl urea, 2-bromo-2-nitropropane-1,3-diol, 1,3-dimethylol-5,5-dimethyl hydrantoin (DMDM hydantoin)), halogens (e.g., 3-iodo-2-propynyl-butylcarbamate (IPBC)), isothiazolinones (e.g., methylchloroisothiazolinone (MCI), methylisothiazolinone (MI), benzothiazolinone, phenoxyethanol used alone or in association with methyldibromo glutaronitrile (MDBGN), glutaronitrile, potassium sorbate, and/or 3-iodo-2-propynyl-butylcarbamate (IPBC), and/or parabens (e.g., methylparaben, ethylparaben, propylparaben, and/or butylparaben). Essential oils may be excluded, particularly from formulations intended for topical application (e.g., the preservative systems of the invention can exclude tea tree, lavender, jasmine, lemon, orange, citronella, cassia, ylang-ylang, aniba rosaeodora, and clover oils).

Uses:

The preservative systems described herein are expected to be useful in protecting various compositions from microbial contamination, and that remains true whether the compositions are formulated for application or administration to a human or another living being. In particular, we wish to emphasize that the preservative systems described herein can be used in veterinary products. The formulations in which the preservative systems are incorporated can be emulsions, liquids, ointments, or gels. In any of the embodiments described herein, the formulation can be a cosmetic product formulated, for example, to cleanse, protect or improve the appearance of the skin, hair, or nails.

Carriers:

The preservative systems described herein can further include one or more carriers and/or one or more inert agents. The carrier can be a water (e.g., deionized water), a solvent such as butylene glycol or phenoxyethanol, or an oil. For example, the oil can be an animal oil or a plant-derived oil (e.g., sesame oil (*Sesamum indicum* seed oil).

The inert agent can be a fat (e.g., a triglyceride such as caprylic capric triglyceride) or a polysaccharide (e.g., xanthan gum).

Production Methods:

The xylitol esters and/or ethers, caprylyl glycol, ethylhexylglycerin, and 1,3-propanediol can simply be mixed together and warmed to about 40-50° C. if necessary to ensure uniformity. This mixture is then added to the water phase of a formulation and heated to the temperature needed for the formulation. This temperature can be as low as room temperature or as high as about 75-80° C.

Assays:

In various embodiments, the preservative systems described herein inhibit contamination caused by gram-negative and/or gram-positive bacteria. Specific microbes that can be inhibited include *Escherichia coli, Pseudomonas aeruginosa, Staphylococcus mareus, Aspergillus niger,* and *Candida albicans.* The preservative systems may also, due to their broad-spectrum activity, inhibit the growth of one or more fungi, parasites, or molds. Antimicrobial properties can be evaluated using various assays known in the art, such as the Cosmetic, Toiletry, and Fragrance Association (CTFA) Microbiology Guidelines. While the invention is not so limited, a preservative system described herein may be deemed effective by virtue of challenge testing. For example, one can employ the CTFA Microbiology Guidelines, Section 20, M-3, A Method for Preservation Testing of Water Miscible Personal Care Products and USP 33, Section 61, Neutralization/Removal of Antimicrobial Activity. The test microorganisms include *S. aureus* (ATCC #6538), *E. coli* (ATCC #8739), and *P. auruginosa* (ATCC #9027), each inoculated into culture at $1\times10^6$ CFU/g and incubated at 30-37° C. as well as *C. albicans* (ATCC #10231), inoculated into culture at $1\times10^5$ CFU/g and incubated at 30-37° C. and *A. niger* (ATCC #16404), inoculated into culture at $1\times10$ CFU/g and incubated at 20-25° C. The microbial count is measured at 1, 2, and 7 days to determine the survival ability of the microorganisms in the preserved test formulations. The preservative system can be deemed effective in the sample examined if: (1) the concentrations of viable bacteria demonstrate no less than 3.0 log reduction (99.9%) from the initial count at 7 days, and no increase for the duration of the test period and (2) the concentration of viable yeast and molds demonstrate no less than a 1.0 log reduction (90.0%) from the initial count at 7 days, and no increase for the duration of the test period.

EXAMPLE 1: MICROBIAL GROWTH INHIBITION

In one example, the preservative components are mixed together in culture to form a mixture with a composition (in weight percentages) of 1.0% xylityl sesquicaprylate, 0.700/% caprylyl glycol, 0.30% ethylhexylglycerin and 3.0% 1,3-propanediol. The mixture is heated to 40-50° C. to ensure uniformity.

The test microorganisms *S. aureus* (ATCC #6538), *E. coli* (ATCC #8739), and *P. auruginosa* (ATCC #9027), were each inoculated into culture at $1\times10^6$ CFU/g and incubated at 30-37° C. *C. albicans* (ATCC #10231) was inoculated into culture at $1\times10^5$ CFU/g and incubated at 30-37° C. and *A. niger* (ATCC #16404) was inoculated into culture at $1\times10^5$ CFU/g and incubated at 20-25° C. The microbial count is measured at 1, 2, and 7 days to determine the survival ability of the microorganisms in the above. For each of these test microorganisms, the preservative system was deemed effective in the sample based on the criteria that:

(1) the concentrations of viable bacteria demonstrated no less than 3.0 log reduction (99.9%) from the initial count at 7 days, and no increase for the duration of the test period and (2) the concentration of viable yeast and molds demonstrate no less than a 1.0 log reduction (90.0%) from the initial count at 7 days, and no increase for the duration of the test period.

What is claimed is:

1. A preservative system comprising xylityl sesquicaprylate, caprylyl glycol, ethylhexylglycerin, and 1,3-propanediol, wherein the xylityl sesquicaprylate is present in the final formulation at 1.0% (w/w); the caprylyl glycol is present in the final formulation at 0.70% (w/w); the ethylhexylglycerine is present in the final formulation at 0.3% (w/w); and the 1,3-propanediol is present in the final formulation at 2.0-4.0% (w/w).

2. The preservative system of claim 1, wherein the system is incorporated into a formulation for administration to a mammal.

3. The preservative system of claim 1, further comprising an alkaloid, an amino acid residue, a steroid, a flavanoid, a flavonoid, a curcuminoid, a coumarin, a quinone, a phenolic compound, a polyphenolic compound, a glycoprotein, a carbohydrate, a terpene, a protein or peptide, or any combination thereof.

4. The preservative system of claim 2, further comprising an alkaloid, an amino acid residue, a steroid, a flavanoid, a flavonoid, a curcuminoid, a coumarin, a quinone, a phenolic compound, a polyphenolic compound, a glycoprotein, a carbohydrate, a terpene, a protein or peptide, or any combination thereof.

5. The preservative system of claim 1, further comprising anisic acid, butylene glycol, caprylhydroxamic acid, a chelating agent, dehydroacetic acid, gluconolactone, glycerin, glyceryl caprylate, glyceryl laurate, glyceryl undecylenate, 1,2-hexanediol, lactoferrin, nisin, pentylene glycol, phenylethyl alcohol, phenoxyethanol, polyaminopropyl biguanide, potassium sorbate, propylene glycol, sodium benzoate, sodium dehydroacetate, phenylpropanol, chlorphenesin, or any combination thereof.

6. The preservative system of claim 2, further comprising anisic acid, butylene glycol, caprylhydroxamic acid, a chelating agent, dehydroacetic acid, gluconolactone, glycerin, glyceryl caprylate, glyceryl laurate, glyceryl undecylenate, 1,2-hexanediol, lactoferrin, nisin, pentylene glycol, phenylethyl alcohol, phenoxyethanol, polyaminopropyl biguanide, potassium sorbate, propylene glycol, sodium benzoate, sodium dehydroacetate, phenylpropanol, chlorphenesin, or any combination thereof.

7. The preservative system of claim 2, wherein the system is formulated for parenteral administration.

8. The preservative system of claim 7, wherein the parenteral administration is topical, subcutaneous, or subdermal administration.

9. The preservative system of claim 1, wherein the xylityl sesquicaprylate is present in the final formulation at 1.0% (w/w); the caprylyl glycol is present in the final formulation at 0.70% (w/w); the ethylhexylglycerine is present in the final formulation at 0.3% (w/w); and the 1,3-propanediol is present in the final formulation at 3.0% (w/w).

10. The preservative system of claim 1, further comprising an active ingredient.

11. The preservative system of claim 2, further comprising an active ingredient.

12. The preservative system of claim 2, wherein the formulation is an emulsion, gel, liquid, ointment, stick, or serum.

13. The preservative system of claim 2, wherein the formulation is an analgesic, antacid, anti-dandruff product, antihistamine, antiperspirant, antiseptic, antitussive, astringent, bronchodilator, cold sore remedy, counterirritant, demulcent, diaper rash cream, diuretic, expectorant, keratolytic, laxative, moisturizer, mouthwash, muscle relaxant, nasal decongestant, shampoo, skin-lightener, sleep aid, sunscreen, topical dermatological product, or wound cleanser.

14. A method of preserving a formulation from microbial contamination comprising including in the formulation xylityl sesquicaprylate, caprylyl glycol, ethylhexylglycerin, and 1,3-propanediol, wherein the xylityl sesquicaprylate is present in the final formulation at 1.0% (w/w); the caprylyl glycol is present in the final formulation at 0.70% (w/w); the ethylhexylglycerine is present in the final formulation at 0.3% (w/w); and the 1,3-propanediol is present in the final formulation at 2.0-4.0% (w/w).

15. The method of claim 14 wherein the formulation is a cosmetic or personal care formulation.

16. A kit in which a preservative system is prepared and packaged for convenient addition to a formulation suitable for use by a consumer or other end user, wherein the preservative system comprises xylityl sesquicaprylate, caprylyl glycol, ethylhexylglycerin, and 1,3-propanediol, wherein the xylityl sesquicaprylate is present in the final formulation at 1.0% (w/w); the caprylyl glycol is present in the final formulation at 0.70% (w/w); the ethylhexylglycerine is present in the final formulation at 0.3% (w/w); and the 1,3-propanediol is present in the final formulation at 2.0-4.0% (w/w).

17. The preservative system of claim 2, wherein the 1,3-propanediol is present in the final formulation at about 2.0-4.0% (w/w).

18. The preservative system of claim 17, wherein the 1,3-propanediol is present in the final formulation at 3.0% (w/w).

19. The preservation system of claim 1, wherein the system is non-toxic or non-irritating.

\* \* \* \* \*